US00PP31510P2

(12) United States Plant Patent
Joppe

(10) Patent No.: US PP31,510 P2
(45) Date of Patent: Mar. 3, 2020

(54) ***CIMICIFUGA JAPONICA* PLANT NAMED 'HILLSIDE SPLASHDANCE'**

(50) Latin Name: *Cimicifuga japonica*
Varietal Denomination: Hillside Splashdance

(71) Applicant: Peter Joppe, Shelburne, MA (US)

(72) Inventor: Peter Joppe, Shelburne, MA (US)

( * ) Notice: Subject to any disclaimer, the term of this patent is extended or adjusted under 35 U.S.C. 154(b) by 0 days.

(21) Appl. No.: 15/932,665

(22) Filed: Apr. 4, 2018

(51) Int. Cl.
*A01H 5/02* (2018.01)
*A01H 6/72* (2018.01)

(52) U.S. Cl.
USPC ..... Plt./263.1

(58) Field of Classification Search
USPC ..... Plt./263.1
See application file for complete search history.

(56) References Cited

U.S. PATENT DOCUMENTS

PP21,727 P2 2/2011 Oudolf
PP24,821 P2 8/2014 Van Noort

OTHER PUBLICATIONS

Bay State Perennial Farm-Woodland wildflowers. https://www.baystateperennial.com/html/woodland_flowers.html. 6 pages. (Year: 2018).*

* cited by examiner

*Primary Examiner* — Susan McCormick Ewoldt
*Assistant Examiner* — Karen M Redden
(74) *Attorney, Agent, or Firm* — C. Nessler

(57) ABSTRACT

A new and distinct cultivar of ornamental plant, *Cimicifuga japonica* 'Hillside Splashdance', which has greenish foliage with multi-colored variegation.

4 Drawing Sheets

Latin name: *Cimicifuga japonica*.
Variety denomination: 'Hillside Splashdance'.

BACKGROUND OF THE INVENTION:

The present invention relates to the new and distinct cultivar of *Cimicifuga* plant, botanically known as *Cimicifuga japonica* and hereinafter referred to by the name 'Hillside Splashdance' or as "new plant." *Cimicifuga japonica* is also botanically known as *Actaea japonica*.

The new plant of the present invention was discovered as a seedling in a flat of seedlings of a species form of *Cimicifuga japonica* in Shelburne, Mass., U.S. by the inventor who has asexually reproduced the new plant and who has cultivated the new plant for the last eight years by division. Asexual propagation by division has determined that the characteristics of the new cultivar are stable; the new plant retains its distinctive characteristics and is reproduced true to type in successive generations.

SUMMARY OF THE INVENTION

*Cimicifuga japonica* 'Hillside Splashdance' is unique from all other *Cimicifuga japonica* cultivars known to the inventor hereof. The plant is distinct in having multicolored variegation of the foliage, compared to known unpatented commercial cultivars, for example, *Cimicifuga japonica* 'Chenju Island Form' plant.

The following are traits of *Cimicifuga japonica* 'Hillside Splashdance' plant that, in combination, distinguish it and make it unique from all other *Cimicifuga japonica* cultivars known to the inventor: The plant has an upright habit with of multi-colored variegation, including white, yellow, and cream colors and various shades of light and dark green. The variegation pattern varies from leaf to leaf. The buds of flowers are creamy white to pink color. Numerous racemes with mildly-fragrant cream colored flowers may be present. The predominately green foliage darkens in its color intensity as the season goes on. The plant is suitable for placing in a garden as an accent or en masse.

By having the variegation described above, the new plant differs from other common unpatented commercial cultivar *Cimicifuga japonica* plants which have plain green foliage, as for example the aforementioned *Cimicifuga japonica* 'Chenju Island Form' plant.

BRIEF DESCRIPTION OF THE DRAWING

The photographs show the overall appearance of the new plant. The colors are as accurate as reasonably possible with color reproductions.

DETAILED BOTANICAL DESCRIPTION OF THE PLANT

The following is a detailed description of the new plant cultivar as observed over the last eight years in a nursery setting in Shelburne, Mass., U.S.

Detailed botanical data was collected from up to 3 year-old plants grown in half gallon pots and from up to 5 year-old plants grown in a garden. The phenotype of the new plant cultivar may vary slightly with different growing environments such as temperature, light, fertility, soil pH, soil moisture and plant maturity levels. The new plant has not been tested under all possible growing conditions. The unknown parent *Cimicifuga japonica* of the new plant is commonly available in commerce and is not known to be patented; it has green un-variegated foliage.

The color determination recited herein is in accordance with the 2007 edition of The Royal Horticultural Society (R.H.S.) Colour Chart except where common dictionary terms are used.

Botanical classification: *Cimicijuga japonica.*

Plant habit: Hardy herbaceous perennial with inverted triangle shape when flowering. Dense and bushy growth habit; moderately vigorous growth. Plants average 76 cm tall and average 40 cm width.

Propagation: By division of rootstock and offsets.

Roots: Fibrous roots are fleshy and branched, typically 1-2 mm in diameter. Most roots are tan color ranging between N59D and 160D. Older plant roots may be more brownish in color, 151A.

Stem/branch: Stems are smooth in texture and round in cross section, typically about 3 mm diameter and 6 to 22 cm in length. The base of the stem is purple N99B, fading to green 142A along the stem length. The node at the petiole at the intersection of branches is purple N79A.

Foliage description:

*Arrangement.*—Alternate, ternately compound, basal leaf.

Figure 1A:
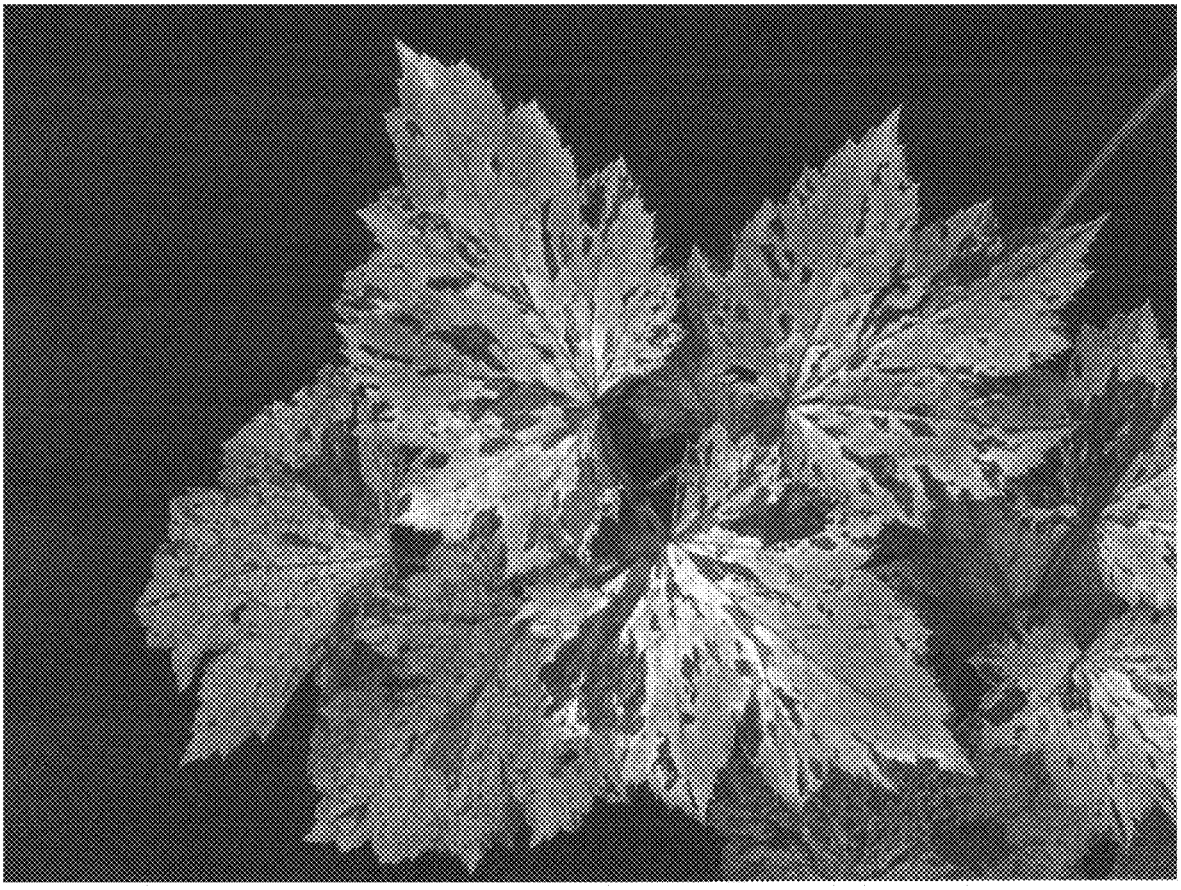
FIG. 1A shows the leaves of a typical new *Cimicifuga japonica* 'Hillside Splashdance' plant, with their variegations.

*Leaf size.*—A typical leaf is 11 to 28 cm in length and 11 to 24 cm in width (excluding the petiole) and is comprised of a multiplicity of leaflets as exemplified by FIG. 1A. Leaflets range in number from 1 to 3, with 3 leaflets being predominant.

*Leaflet.*—A typical leaflet is 5 to 12 cm in length and 11 to 24 cm in width; its shape is broad ovate to orbicular and it has 3 to 5 lobes. A typical leaflet is serrate, glabrous, slightly rugose, and has pinnate veining.

Figure 1B:
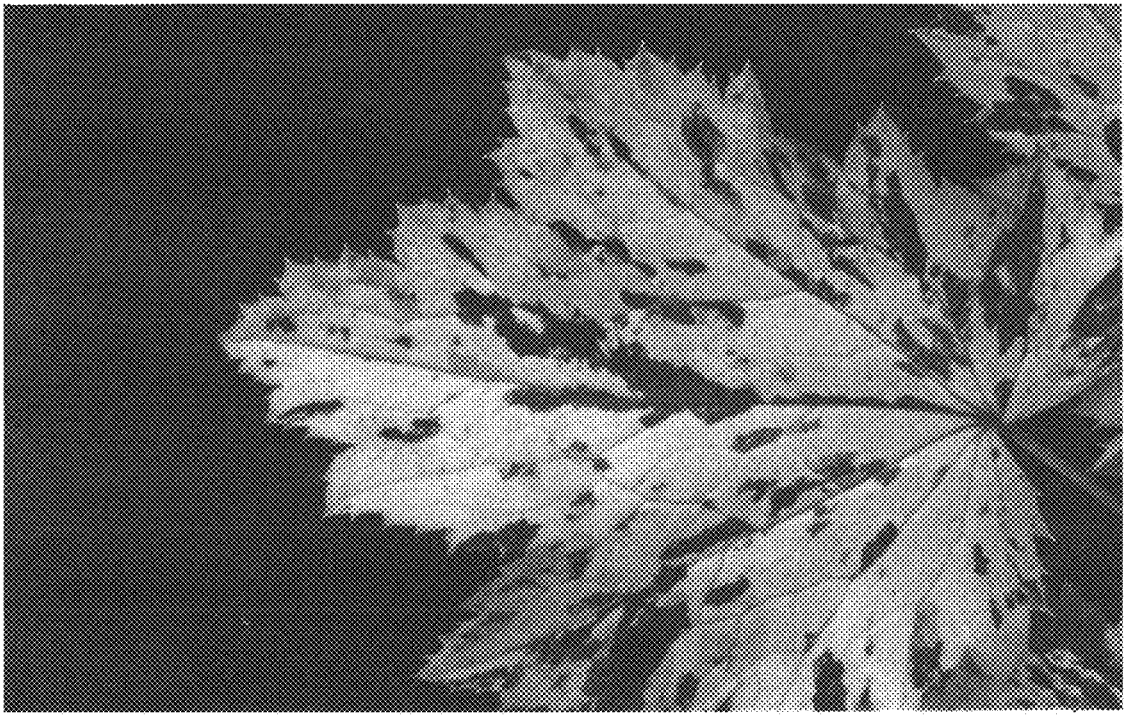
FIG. 1B shows a variegated leaf of another typical new plant where cream color dominates dark green color.
Figure 2:
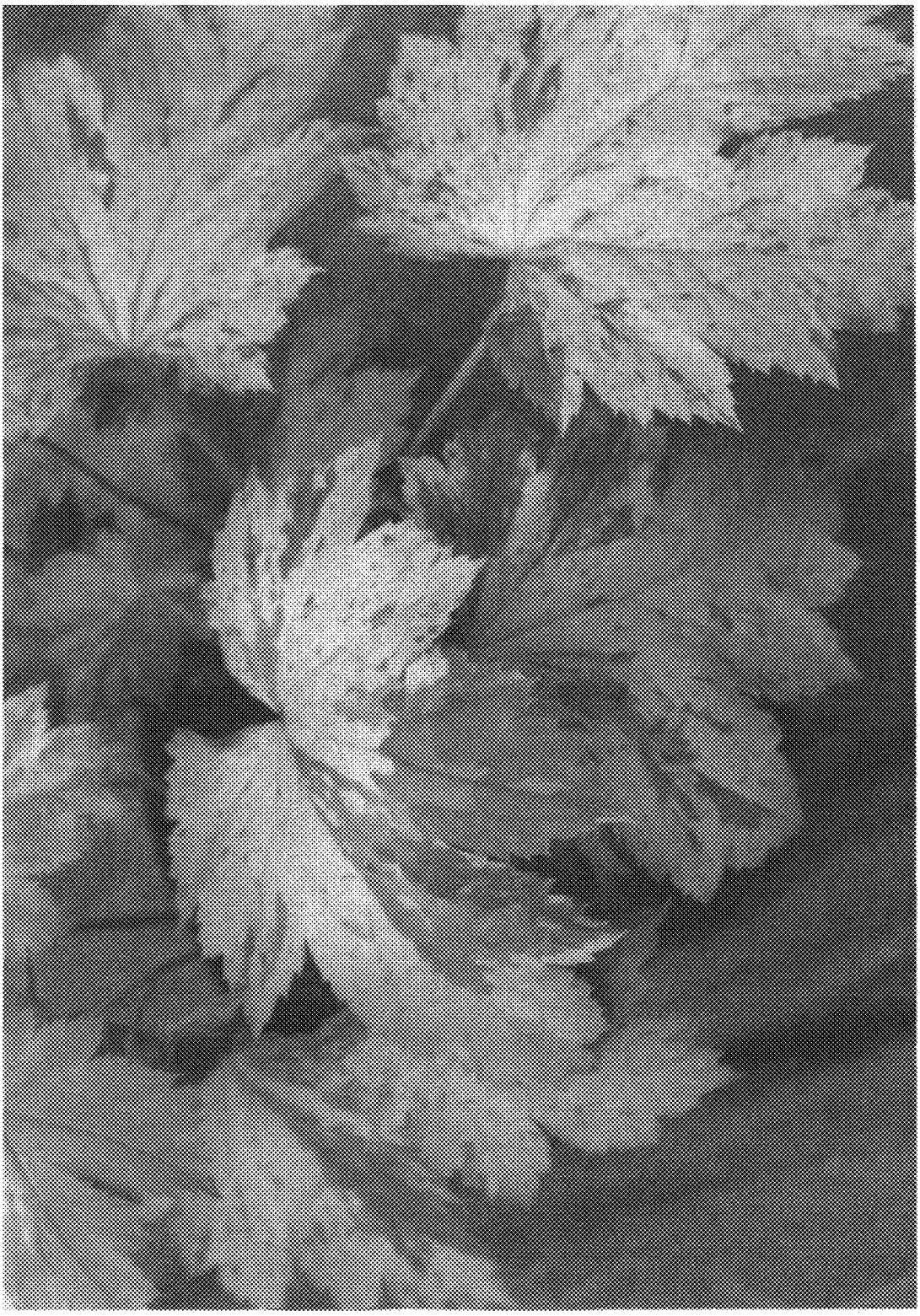
FIG. 2 shows a multiplicity of variegated leaves of a typical new plant as presented in Springtime, with cream, warm yellow and bright green colors.

*Leaf color.*—Early spring leaves are green 142A; developing leaves become variegated, having greenish yellow and green colors ranging between RHS 149B and 141C. Some leaves will tend to be solid green, having colors of RHS 135A and RHS 134A. As time passes and the days warm up, variegation emerges which has contrasting colors of warm yellow green 149C and green 140A. See FIG. 2. During mid-summer and late summer the leaves predominately tend to become a darker green color 136B; and the warm yellow portions turn to light green 142A. A few leaves become off-white ranging between 150D and NN155D. See FIG. 1B. Late in the summer season, variegation may become splotchy. The lower leaf color of emerging young leaves is green 142A; the lower leaf color of mature leaves is light green, ranging between 134C and 134D.

*Leaf petiole.*—Average Primary petiole is 12 cm long by 3 mm wide; average secondary petiole is 6 cm long by 2 mm wide. Petioles have green colors ranging between 142A and 149C with intersections of dark purple N79A.

Figure 3:
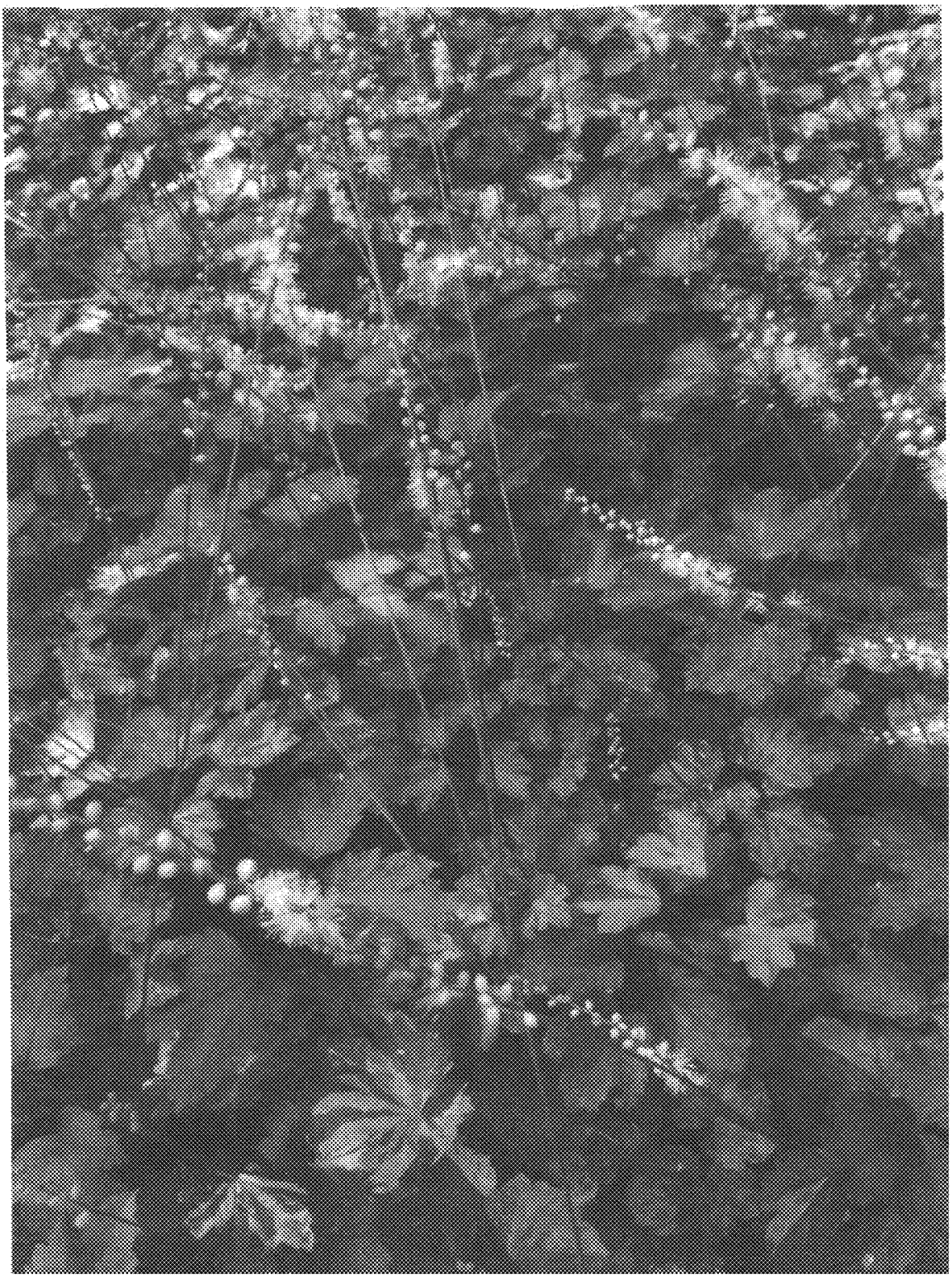
FIG. 3 shows a portion of a new plant having variegated leaves, white and pink unopened flower buds, along with some blossoms which are most often white, less often pink color, as presented in late Summer.
Figure 4:
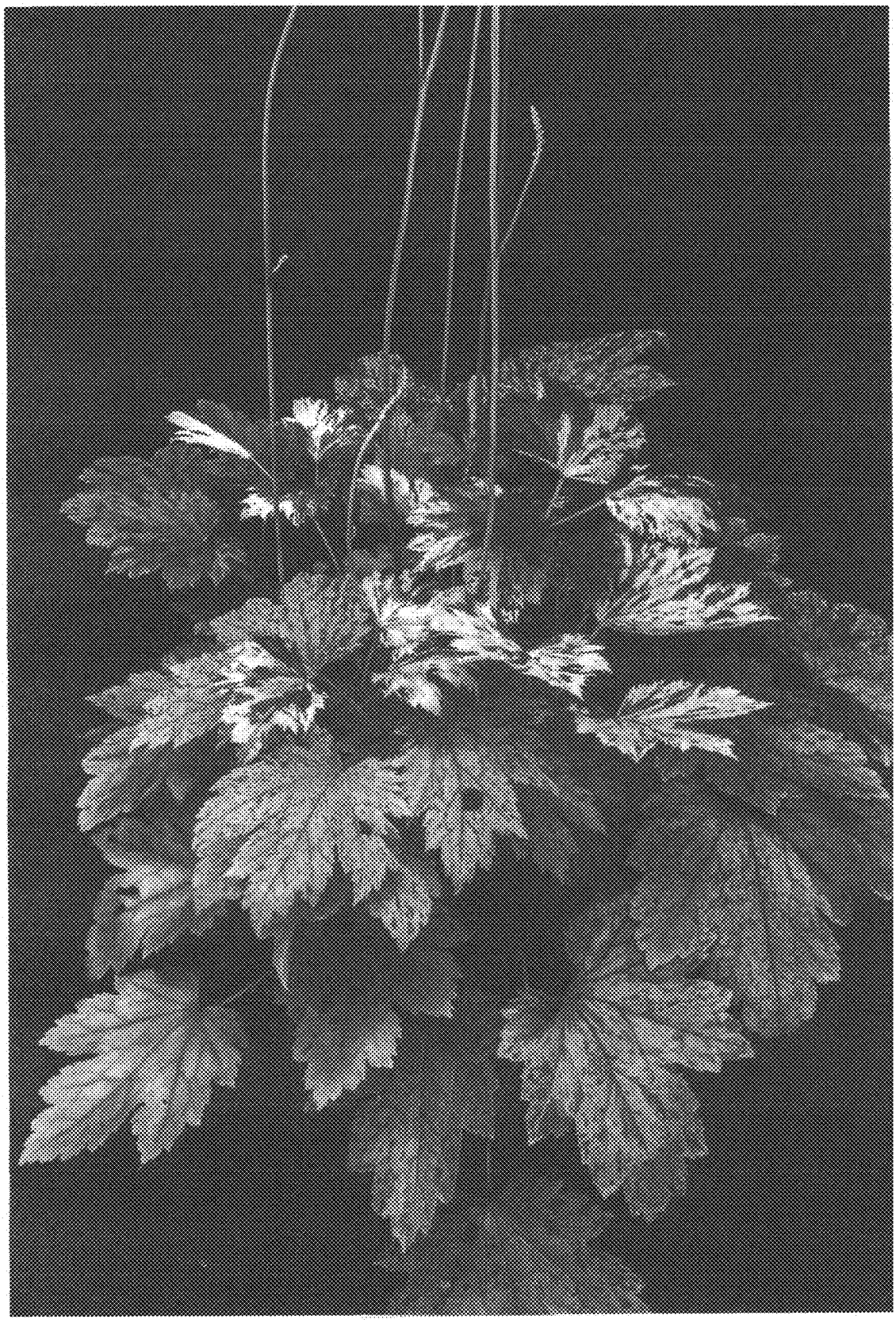
FIG. 4 shows almost all of a full-grown new plant with a typical shape and variegated leaves having different shades of green color.

Flower description:

*Bloom.*—Rotate flowers about 10 to 15 mm in diameter appear once each year beginning in late August, continuing through mid-September in Shelburne Mass. (approximately latitude 42.6 degree N, longitude 72.7 degree E), with flowers lasting from 2-3 weeks. See FIG. 3. Fragrance when present is mild.

*Raceme.*—Average size is 15 cm long (excluding peduncle of 45 to 100 cm long) and 2 cm wide; averaging 60 flowers per primary peduncle; averaging 25 flowers per secondary peduncle; averaging 6 secondary peduncles per primary peduncle.

*Peduncles.*—Average 4 peduncles per plant. Peduncle color: dark gray-green N137C. Color of flower stalks: light green 142A. As buds mature and open the peduncles turn purple, ranging between 79A and 79D.

*Pedicles.*—Average length is 1 to 2 mm by about 2 mm diameter; color is light tan ranging between 158B and 158C.

*Petals.*—None were observed.

*Buds.*—Two sepals enclose the reproductive portion of the flower, forming a bud which is globular and about 3.5 to 5 mm in diameter; typically pink color 75C. Some buds may be cream color, ranging between 157D and NN155A. See FIG. 3.

Reproductive organs: Sepals separate revealing white stamens topped with ovate anthers that are 1 to 2 mm long by 1 mm wide. White stamen filaments are 4 to 5 mm long and less than 1 mm wide. There are 40-50 stamens that surround the white carpel in the center of the flower. The carpel is 2 mm in diameter and 2.5 mm long. The pollen color is white, lighter than NN155D.

Seed/fruit: A single seed pod forms at each point along the raceme where there was once a flower. Ripening seed pods are fleshy and green N141C, 7 to 8 mm long and 3 to 5 mm wide. When the seed is ripe, the outer shell dries out, becomes paper thin, and turns brown N199A. There are 2-4 seeds per pod. The seeds are brown 199B and pubescent, about 1 to 2 mm wide and 3 mm long.

Garden performance: The new plant has been observed to have good garden performance. The new plant grows best in part or light shade with ample moisture and adequate drainage. Hardy to USDA zone 4.

The invention claimed is:

1. A new and distinct cultivar of *Cimicifuga japonica* plant named 'Hillside Splashdance' as herein described and illustrated.

* * * * *